(12) United States Patent
Aquino et al.

(10) Patent No.: US 6,452,023 B1
(45) Date of Patent: Sep. 17, 2002

(54) PROCESS FOR PREPARING D,L-α-TOCOPHEROL

(75) Inventors: Fabrice Aquino, Reiningue (FR); Werner Bonrath, Freiburg (DE)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/342,272

(22) Filed: Jun. 29, 1999

(30) Foreign Application Priority Data

Jul. 10, 1998 (EP) .............................................. 98112842

(51) Int. Cl.⁷ .............................................. C07D 311/72
(52) U.S. Cl. ........................................ 549/408; 549/412
(58) Field of Search .................................. 549/408, 412

(56) References Cited

FOREIGN PATENT DOCUMENTS

| EP | 0694 541 | 1/1996 |
|---|---|---|
| WO | WO 97/28151 | 8/1997 |

OTHER PUBLICATIONS

Kozhevnikov, I.V. , et al., *React. Kinet. Catal. Lett.* 47(1), 59–64 (1992).

Jansen, R.J.J., et al., *Recl. Trav. Chim. Pays–Bas* 113, 115–135 (1994).

*Primary Examiner*—T. A. Solola
(74) *Attorney, Agent, or Firm*—Bryan Cave LLP

(57) ABSTRACT

A process for the manufacture of d,l-α-tocopherol by the acid-catalyzed condensation of trimethylhydroquinone with isophytol or phytol in ethylene or propylene carbonate or a mixture of both carbonates, or in a mixture of one or both of the carbonates and a non-polar solvent, comprises carrying out the condensation in the presence of at most 0.4 weight percent based on the weight of isophytol or phytol of 12-tungstophosphoric acid, 12-molybdophosphoric acid or 12-tungstosilicic acid. The product of the process is the most active and industrially important member of the vitamin E group.

23 Claims, No Drawings

PROCESS FOR PREPARING D,L-α-TOCOPHEROL

SUMMARY

The present invention is concerned with a novel process for the manufacture of d,1-α-tocopherol by the acid-catalyzed condensation of trimethylhydroquinone (TMHQ) with isophytol (IP) or phytol (PH) in a solvent. As is known, d,1-α-tocopherol is a diastereoisomeric mixture of 2,5,7,8-tetramethyl-2-(4',8',12'-trimethyl-tridecyl)-6-chromanol (α-tocopherol), which is the most active and industrially most important member of the vitamin E group.

BACKGROUND OF THE INVENTION

Many processes for the manufacture of d,1-α-tocopherol by the condensation of TMHQ with IP or PH in the presence of a catalyst or catalyst system and in a solvent or solvent system are described in the literature. These processes go back to the work of Karrer et al., Bergel et al., as well as, Smith et al. [see Helv. Chim. Acta 21, 520 et seq. (1938), Nature 142, 36 et seq. (1938) and, respectively, Science 88, 37 et seq. (1938) and J. Am. Chem. Soc. 61, 2615 et seq. (1939)]. While Karrer et al., carried out the synthesis of d,1-α-tocopherol from TMHQ and phytyl bromide in the presence of anhydrous zinc chloride ($ZnCl_2$; a Lewis acid), Bergel et al. and Smith et al. used TMHQ and PH as starting materials. In the following years many modifications, e.g., alternative solvents and Lewis acids, were developed. From the work of Karrer et al., a technically interesting process for the manufacture of d,1-α-tocopherol was developed in 1941 that was based on the condensation of TMHQ with IP in the presence of the catalyst system $ZnCl_2$/hydrochloric acid (HCl). See, U.S. Pat. No. 2,411,969. Later publications, e.g., Japanese Patent Publications (Kokai) 54380/1985, 64977/1985 and 226979/1987 [Chemical Abstracts (C.A.) 103, 123731s (1985), C.A. 103, 104799d (1985) and, respectively, C.A. 110, 39217r (1989)], describe this condensation in the presence of zinc and/or $ZnCl_2$ and a Bronsted (protonic) acid, such as a hydrohalic acid, e.g., HCl, trichloroacetic acid, acetic acid and the like, especially $ZnCl_2$/HCl, as the catalyst system. Disadvantages of these and further published processes featuring $ZnCl_2$ in combination with a Bronsted acid are the corrosive properties of the acids and the contamination of the waste water with zinc ions as a result of the large amount of $ZnCl_2$ required for the catalysis.

The manufacture of d,1-α-tocopherol by the reaction of TMHQ with phytyl chloride, PH or IP in the presence of boron trifluoride ($BF_3$) or its etherate ($BF_3.Et_2O$) is described in German Patents 960720 and 1015446 as well as in U.S. Pat. No. 3,444,213. However $BF_3$ also has corrosive properties.

Also, the condensation of TMHQ with IP or PH in the presence of a Lewis acid, e.g., $ZnCl_2$, $BF_3$ or aluminium trichloride ($AlCl_3$), a strong acid, e.g., HCl, and an amine salt as the catalyst system is described in European Patent Publication (EP) 100471. In an earlier German patent publication (Deutsche Offenlegungsschrift: DOS), No. 2606830, the IP or PH is pretreated with ammonia or an amine before the condensation with TMHQ in the presence of $ZnCl_2$ and an acid is effected. In both cases corrosion problems occur.

A further interesting method for the manufacture of d,1-α-tocopherol from TMHQ and IP comprises using an isolated TMHQ-$BF_3$or -$AlCl_3$ complex and a solvent mixture featuring a nitro compound (DOS 1909164). This process avoids to a large extent the formation of undesired by-products because it involves mild reaction conditions. The yield of d,1-α-tocopherol, based on IP and the use of the solvent mixture methylene chloride/nitromethane, is given as 77%. However, these days the use of such a halogenated hydrocarbon as methylene chloride as a solvent is less tolerated than hitherto for ecological reasons.

The manufacture of d,1-α-tocopherol by the condensation of TMHQ with IP using cation exchange resin complexes of metal ions ($Zn^{2+}$, $Sn^{2+}$ and $Sn^{4+}$) is disclosed in Bull. Chem. Soc. Japan 50, 2477–2478 (1977); amongst its disadvantages are that it produces the product in unsatisfactory yields.

The use of macroreticular ion exchangers, e.g., Amberlyst® 15, as the catalyst for the condensation of TMHQ with IP is described in U.S. Pat. No. 3,459,773. However, the d,1-α-tocopherol could not be obtained in the requisite purity.

EP 603695 describes the manufacture of d,1-α-tocopherol in liquid or supercritical carbon dioxide by the condensation of TMHQ with IP or PH in the presence of acidic catalysts, such as $ZnCl_2$/HCl and ion exchangers. The reported yields are unsatisfactory.

The condensation in the presence of a catalyst system which consists of iron(II) chloride, metallic iron and HCl gas or aqueous solution is described in DOS 2160103 and U.S. Pat. No. 3,789,086. The formation of less by-products is advantageous compared with the aforementioned process using $ZnCl_2$/HCl. However, corrosion problems and chloride contamination are equally disadvantageous.

An interesting alternative for the condensation of TMHQ with IP to d,1-α-tocopherol comprises using trifluoroacetic acid or its anhydride as the catalyst, see, EP 12824. Although the avoidance of HCl is achieved in this process, the catalyst is relatively expensive.

The use of the heteropoly acid 12-tungstophosphoric or 12-tungstosilicic acid as the catalyst for the condensation of TMHQ with IP was described for the first time in React. Kinet. Catal. Lett. 47(1), 59–64 (1992). Following this procedure, d,1-α-tocopherol could be obtained, using various solvents, in about 90% yield.

A further process described in the literature [EP 658552; Bull. Chem. Soc. Japan 68, 3569–3571 (1995)] for the synthesis of d,1-α-tocopherol is based on the use of a scandium, yttrium or lanthanide fluorosulphonate, nitrate or sulphate, e.g., scandium trifluoromethanesulphonate. With up to about 10% excess of IP, this process gives yields up to 98%.

The use of ion-exchanged bentonite, montmorillonite or saponite through treatment with, e.g., scandium chloride and other metal salts (yttrium, lanthanum, etc.) as the catalyst for the condensation of TMHQ with IP or PH is disadvantageous because of the need for a large amount of catalyst [EP 677520; Bull. Chem. Soc. Japan 69, 137–139 (1996)].

According to the Examples of EP 694 541, the condensation of TMHQ with IP to α-tocopherol can be achieved in high yields and with a high product purity when solvents such as carbonate esters, fatty acid esters and mixed solvent systems are employed with catalysis being effected by $ZnCl_2$/HCl. Disadvantages in this process include the contamination of the waste water by zinc ions and the usual large "catalyst amount" of $ZnCl_2$ used.

According to WO 97/28151, the acid-catalysed condensation of TMHQ with IP can be performed in a cyclic carbonate or α-lactone as the solvent. The preferred catalyst is a mixture of ortho boric acid and oxalic, tartaric or citric acid, or boron trifluoride etherate.

From the foregoing, it is evident that most of the previously known processes have considerable disadvantages. Corrosion problems occur in all processes in which acid catalysts such as boron trifluoride are used. Toxicity problems with the boron trifluoride adducts also occur, and, when iron or zinc is used, there is a contamination of the waste water with the metal ions that is no longer acceptable. In some processes, the formation of undesired by-products, e.g., phytyltoluene and chlorophytols, is an especially serious problem.

DETAILED DESCRIPTION OF THE INVENTION

An object of the present invention is to provide a process for the manufacture of d,1-α-tocopherol by the condensation of trimethylhydroquinone with isophytol or phytol in the presence of a catalyst and in a solvent without the disadvantages of previously known procedures. In this respect, it is necessary that the catalyst used has no, or at least a much reduced, corrosive action, is non-toxic, does not contaminate the environment and catalyzes the desired reaction as selectively as possible and in high yields. Furthermore, the catalyst should display its activity in small, really catalytic, amounts and should be readily separable and re-usable several times.

This object of the present invention is achieved by carrying out the condensation of trimethylhydroquinone with isophytol or phytol in the presence of at most 0.4 weight percent, based on the weight of isophytol or phytol, of 12-tungstophosphoric acid ($H_3PW_{12}O_{40}$), 12-molybdophosphoric acid ($H_3PMo_{12}O_4$) or 12-tungstosilicic acid ($H,SiW_{12}O_{40}$) as the catalyst. Moreover, the condensation is effected in ethylene or propylene carbonate or a mixture of both carbonates, or in a mixture of one or both of the carbonates and a non-polar solvent, as the solvent or solvent system, as appropriate.

The condensation itself is represented in the following Reaction Scheme, showing the reaction with IP only.

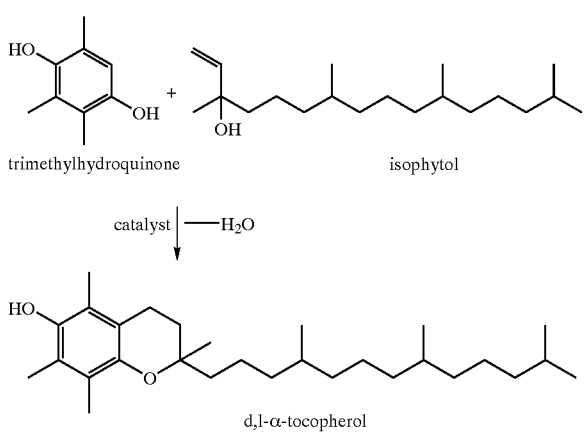

Accordingly, the process in accordance with the invention for the manufacture of d,1-α-tocopherol by the acid-catalyzed condensation of trimethylhydroquinone with isophytol or phytol in ethylene or propylene carbonate or a mixture of both carbonates, or in a mixture of one or both of the carbonates and a non-polar solvent, is characterized by carrying out the condensation in the presence of at most 0.4 weight percent, based on the weight of isophytol or phytol, of 12-tungstophosphoric acid, 12-molybdophosphoric acid or 12-tungstosilicic acid as the acid catalyst.

If in addition to ethylene or propylene carbonate or a mixture of both carbonates a non-polar solvent is employed, it is selected from hexane, heptane or octane, preferably it is heptane.

The condensation is conveniently effected at temperatures from about 50° C. to about 150° C., preferably from about 70° C. to about 130° C., especially at about 100° C.

Furthermore, trimethylhydroquinone is conveniently used in a molar excess of about 30 to 120%, preferably about 50 to 100%, over the amount of isophytol or phytol used. A particular range is about 30 to 65% molar excess. The advantage of using a relatively large, e.g., up to about 120%, molar excess of trimethylhydroquinone is that an efficient process operation involves a continuous recycling of the unreacted trimethylhydroquinone into the reaction medium.

The amount of acid catalyst is conveniently about 0.1 to 0.4 weight percent, preferably about 0.35 weight percent, based on the weight of isophytol or phytol.

If the reaction is carried out in the presence of both a carbonate (ethylene or propylene carbonate, or both) and a non-polar solvent, then the volume ratio of the non-polar solvent to the carbonate used in the two-phase solvent system is about 0.3:1 to 5:1, preferably about 1:1 to 3:2. The total amount of solvent, i.e., carbonate(s) and, optionally, also a non-polar solvent, is such that about 10 to 100 ml, preferably about 50 to 80 ml, for example about 30 to 60 ml, of carbonate(s) are used per 100 mmol of trimethylhydroquinone, and, optionally, about 10 to 150 ml, preferably about 25 to 100 ml, of non-polar solvent are used per 100 mmol of isophytol or phytol. In any event, only the one or the other carbonate is preferably used, either as the sole solvent or as the carbonate component of the solvent system with the non-polar solvent. As the latter, heptane is preferably employed, and the carbonate itself is preferably ethylene carbonate.

Moreover, the condensation is conveniently carried out under an inert gas atmosphere, preferably gaseous nitrogen or argon.

As the acid catalyst, 12-tungstophosphoric acid or 12-tungstosilicic acid is preferably used.

The process in accordance with the invention can be carried out operationally in a very simple manner by adding isophytol or phytol or a solution thereof in the optionally employed non-polar solvent dropwise to a solution or suspension of the trimethylhydroquinone and the acid catalyst in ethylene or propylene carbonate or a mixture of both carbonates. The rate at which the isophytol or phytol is added is not critical. Conveniently, however, isophytol or phytol or the solution thereof is added dropwise over a period of 0.1 to 3, preferably 0.3 to 2.0, hours. After completion of the isophytol or phytol addition and an appropriate subsequent condensation, during which it is advantageous to remove the resulting water by azeotropic distillation or in the flow of inert gas used, isolation and purification of the obtained d,1-α-tocopherol can be effected by procedures conventionally used in organic chemistry, e.g., by distillation. The process can be carried out batchwise or continuously.

Particular advantages of using the acid catalyst in the process in accordance with the invention are, in addition to high yields of d,1-α-tocopherol, avoiding corrosion, avoiding waste water contamination with heavy metal ions, the high selectivity as well as the ready isolation of d,1-α-tocopherol from the mixture after reaction.

The process in accordance with the invention is illustrated by the following Examples:

EXAMPLES 1–22

To a mixture of 23.3 g (150 mmol) of 2,3,5-trimethylhydroquinone (98% pure), 80 ml of ethylene carbonate or propylene carbonate (in each case 99% pure) and 150 mg of the heteropoly acid, 31.21 g (100 mmol) of isophytol (95% pure) either alone or in solution in up to 100 ml of heptane (or hexane or octane) were added dropwise under an argon atmosphere and with stirring at 70° C. to 140° C., according to solvent, over a period of 20 to 120 minutes ("feed IP"). During the addition of isophytol, an azeotropic mixture of water/heptane (or water/hexane or water/octane) was separated with the help of a water separator. After completion of the addition, the reaction mixture was heated under stirring at 140° C. for another 30 minutes. The resulting two-phase system was cooled to 80° C. and 100 ml of heptane (or hexane or octane) were added. The phases were separated and the carbonate layer was re-used. The heptane (or hexane or octane) layer was concentrated under reduced pressure to afford d,1-α-tocopherol as a brown oil. The results of the various trials are summarized in the following Tables 1 and 2.

TABLE 1

Condensation reaction between TMHQ and IP catalyzed by different heteropoly acids.

| Ex. | Solvent | Catalyst (g/100 g product) | React, Temp. (° C). | Feed IP (min) | Yield (%)[a] | Purity %[b] |
|---|---|---|---|---|---|---|
| 1 | EC | HPW (0.35) | 140 | 30 | 92.0 | 88.4 |
| 2 | EC | HPW (0.35) | 140 | 60 | 93.4 | 90.9 |
| 3 | EC | HPW (0.35) | 140 | 90 | 94.4 | 93.0 |
| 4 | EC | HPW (0.35) | 140 | 120 | 95.3 | 91.3 |
| 5 | PC | HPW (1.13) | 140 | 30 | 94.4 | 85.5 |
| 6 | EC + Hep | HPW (0.35) | 100 | 20 | 96.4 | 92.1 |
| 7 | EC + Hep | HPW (0.35) | 100 | 30 | 95.1 | 87.8 |
| 8 | EC + Hep | HPW (0.35) | 100 | 60 | 95.7 | 91.3 |
| 9 | EC + Hep | HPW (0.35) | 100 | 90 | 96.0 | 90.7 |
| 10 | EC + Hep | HPW (0.35) | 100 | 120 | 97.6 | 91.8 |
| 11 | EC + Hep | HSiW (0.35) | 100 | 20 | 96.6 | 91.8 |
| 12 | EC + Hep | HPMo (0.35) | 100 | 20 | 94.1 | 89.4 |

[a]isolated yield (not optimized), [b]determined by gas-liquid chromatographical (GLC) analysis of the isolated products (int. standard), EC = ethylene carbonate, PC = propylene carbonate, Hep = heptane (in each case 100 ml used), HPW = $H_3PW_{12}O_{40}$, HSiW = $H_4SiW_{12}O_{40}$, HPMo = $H_3PMo_{12}O_{40}$.

TABLE 2

Condensation reaction between TMHQ and IP catalyzed by HPW with different amounts of non-polar solvent (in each case feed IP = 30 min.)

| Ex. | Non-polar solvent | ml* | React. temp. (° C.) | Yield (%)[a] | Purity (%)[b] |
|---|---|---|---|---|---|
| 13 | — | 0 | 140 | 92.0 | 88.4 |
| 14 | Hexane | 25 | 70 | 95.4 | 92.0 |
| 15 | Hexane | 50 | 70 | 94.8 | 92.0 |
| 16 | Hexane | 100 | 70 | 97.0 | 91.4 |
| 17 | Heptane | 25 | 100 | 93.4 | 89.0 |
| 18 | Heptane | 50 | 100 | 96.8 | 89.0 |
| 19 | Heptane | 100 | 100 | 96.4 | 92.1 |
| 20 | Octane | 25 | 127 | 93.0 | 85.7 |
| 21 | Octane | 50 | 127 | 94.1 | 87.0 |
| 22 | Octane | 100 | 127 | 93.2 | 83.9 |

*based on 100 mmol TMHQ, [a]isolated yield (not optimized), [b]determined by GLC analysis of the isolated products (int. standard).

EXAMPLES 23–28

To a mixture of 23.3 g (150 mmol) of 2,3,5-trimethylhydroquinone (98% pure), 80 ml of ethylene carbonate (99% pure), 25 to 100 ml of hexane or heptane and 150 mg of 12-tungstophosphoric acid, 31.21 g (100 mmol) of isophytol (95%) were added dropwise under stirring at 70° C. or 100° C. over a period of 30 minutes. After completion of the addition, the reaction mixture was stirred at this temperature for another 30 minutes while removing the heptane (or hexane). The resulting two-phase-system was cooled to 80° C. (or 60° C.) and 100 ml of heptane (or hexane) were added. The phases were separated and the carbonate layer was re-used. The heptane (or hexane) layer was concentrated under reduced pressure to afford d,1-α-tocopherol as a brown oil. The results of the various trials are summarized in the following Table 3.

TABLE 3

Condensation reaction between TMHQ and IP catalyzed by HPW wherein IP is added without solvent

| Ex. | Non-polar solvent | ml* | React. Temp. (° C.) | Yield (%)[a] | Purity (%)[b] |
|---|---|---|---|---|---|
| 23 | Hexane | 25 | 70 | 96.1 | 91.3 |
| 24 | Hexane | 50 | 70 | 96.8 | 92.0 |
| 25 | Hexane | 100 | 70 | 96.5 | 91.6 |
| 26 | Heptane | 25 | 100 | 93.8 | 88.2 |
| 27 | Heptane | 50 | 100 | 96.3 | 88.3 |
| 28 | Heptane | 100 | 100 | 96.9 | 89.3 |

*based on 100 mmol TMHQ, [a]isolated yield (not optimized), [b]determined by GLC analysis of the isolated products (int. standard).

What is claimed is:

1. A process for making d,l-α-tocopherol by acid-catalyzed condensation, the process comprising reacting trimethylhydroquinone with a phytol, which is selected from the group consisting of isophytol, phytol, and a mixture thereof in a carbonate, which is selected from the group consisting of ethylene carbonate, propylene carbonate, a mixture of ethylene carbonate and propylene carbonate, a mixture of ethylene carbonate and a non-polar solvent, a mixture of propylene carbonate and a non-polar solvent, and a mixture of ethylene carbonate, propylene carbonate, and a non-polar solvent, in the presence of at most 0.4 weight percent, based on the weight of the phytol, of an acid catalyst, which is selected from the group consisting of 12-tungstophosphoric acid, 12-molybdophosphoric acid, and 12-tungstosilicic acid.

2. The process of claim 1, wherein the acid catalyst is selected from the group consisting of 12-tungstophosphoric acid and 12-tungstosilicic acid.

3. The process of claim 1, wherein the amount of acid catalyst is about 0.1 to 0.4, based on the weight of the phytol.

4. The process of claim 3, wherein the amount of acid catalyst is about about 0.35 weight percent, based on the weight of the phytol.

5. The process of claim 1, wherein the carbonate is selected from the group consisting of ethylene carbonate and a mixture of ethylene carbonate and a non-polar solvent.

6. The process of claim 1, wherein the non-polar solvent is selected from the group consisting of hexane, heptane, and octane.

7. The process of claim 6, wherein the non-polar solvent is heptane.

8. The process of claim 1, wherein the volume ratio of the non-polar solvent to carbonate is from 0.3:1 to 5:1.

9. The process of claim 8, wherein the volume ratio of the non-polar solvent to carbonate is from 1:1 to 3:2.

10. The process of claim 1, wherein the condensation is effected at temperatures from about 50° C. to about 150° C.

11. The process of claim 10, wherein the condensation is effected at temperatures from about 70° C. to about 130° C.

12. The process of claim 11, wherein the condensation is effected at a temperature of about 100° C.

13. The process of claim 1, wherein trimethylhydroquinone is used in a molar excess of about 30 to 120% over the phytol.

14. The process of claim 13, wherein the molar excess is about 50 to 100%.

15. The process of claim 13, wherein the molar excess is about 30 to 65%.

16. The process of claim 1, wherein about 10 to 100 ml of carbonate selected from the group consisting of ethylene carbonate, propylene carbonate and a mixture of ethylene and propylene carbonate are used per 100 mmol of trimethylhydroquinone.

17. The process of claim 16, wherein about 50 to 80 ml of carbonate are used per 100 mmol of trimethylhydroquinone.

18. The process of claim 16, wherein about 30 to 60 ml of carbonate are used per 100 mmol of trimethylhydroquinone.

19. The process of claim 16, wherein about 10 to 150 ml of the non-polar solvent are used per 100 mmol of phytol.

20. The process of claim 19, wherein about 25 to 100 ml of the non-polar solvent are used per 100 mmol of phytol.

21. The process of claim 1, wherein the phytol or a solution thereof in the non-polar solvent is added dropwise to a solution or suspension of trimethylhydroquinone and the acid catalyst in the carbonate selected from the group consisting of ethylene carbonate, propylene carbonate and a mixture of ethylene and propylene carbonate.

22. The process of claim 1, wherein the water resulting in the condensation is removed by a process selected from the group consisting of azeotropic distillation and use of inert gas in the flow.

23. The process of claim 1, wherein the process carried out is selected from the group consisting of batchwise and continuous.

* * * * *